United States Patent [19]

Bosley, Jr. et al.

[11] Patent Number: 5,081,997

[45] Date of Patent: Jan. 21, 1992

[54] ECHOGENIC DEVICES, MATERIAL AND METHOD

[75] Inventors: Rodney W. Bosley, Jr., Bloomington; Paul G. Thomson, Fillmore; Thomas L. Foster, Poland, all of Ind.

[73] Assignee: Vance Products Incorporated, Spencer, Ind.

[21] Appl. No.: 383,174

[22] Filed: Jul. 20, 1989

Related U.S. Application Data

[63] Continuation-in-part of Ser. No. 320,967, Mar. 9, 1989, abandoned.

[51] Int. Cl.$^5$ .............................................. A61B 8/00
[52] U.S. Cl. .......................... 128/662.02; 128/662.05; 128/754; 128/654
[58] Field of Search ..................... 128/662.05, 662.02, 128/654, 660.07, 754; 356/243

[56] References Cited

U.S. PATENT DOCUMENTS

| | | | |
|---|---|---|---|
| 3,605,750 | 9/1971 | Sheridan et al. | 128/348 |
| 4,111,190 | 9/1978 | Plumridge | 128/2 A |
| 4,277,367 | 7/1981 | Madsen et al. | 252/408 |
| 4,322,164 | 3/1982 | Shaw et al. | 356/243 |
| 4,386,612 | 6/1983 | Roder et al. | 128/660 |
| 4,401,124 | 8/1983 | Guess et al. | 128/660 |
| 4,490,139 | 12/1984 | Huizenga et al. | 604/57 |
| 4,567,896 | 2/1986 | Barnea et al. | 128/660 |
| 4,582,061 | 4/1986 | Fry | 128/329 R |
| 4,718,433 | 1/1988 | Feinstein | 128/662.02 |
| 4,805,628 | 2/1989 | Fry et al. | 168/662.02 |
| 4,869,259 | 9/1989 | Elkins | 128/662.05 |

FOREIGN PATENT DOCUMENTS

84/02838 8/1984 World Int. Prop. O. .

Primary Examiner—Francis Jaworski
Assistant Examiner—George Manuel
Attorney, Agent, or Firm—Richard J. Godlewski

[57] ABSTRACT

Echogenic medical devices and methods of fabrication and of use are disclosed. The devices are adapted to be inserted into a patient. The device includes an elongated member including a material having an acoustic impedance different from that of the surrounding medium. The medium includes surrounding biological tissue or fluids surrounding the member when inserted into a passageway of the patient. The acoustic impedance of the elongated member is sufficiently different from the surrounding medium for enhancing an image produced in response to a sonic beam produced from imaging equipment. The elongated member also includes an interface including the outside surface of the member and a plurality of partially spherical indentations therein. Alternatively, generally spherical particles are attached to the surface of the member for producing the image in response to the sonic beam. Materials such as stainless steel, plastic, and glass are utilized in the manufacture of the medical device. The device may also include an echogenic body member including a composite material echogenically imageable in the patient. The composite material includes a matrix material with discrete sound reflective particles made from a material different from the matrix material and embedded therein. Several sound reflective particles are disclosed, one type of particle being a glass microsphere about 5 microns in diameter. The matrix material may be a plastic, and may be formed or extruded into devices such as catheters or other medical devices. The composite material may include different quantities of sound reflective particles by percent volume. Furthermore, a radiopaque material may be included in the composite material so the medical device is both ultrasonically imageable and radiographically imageable.

98 Claims, 8 Drawing Sheets

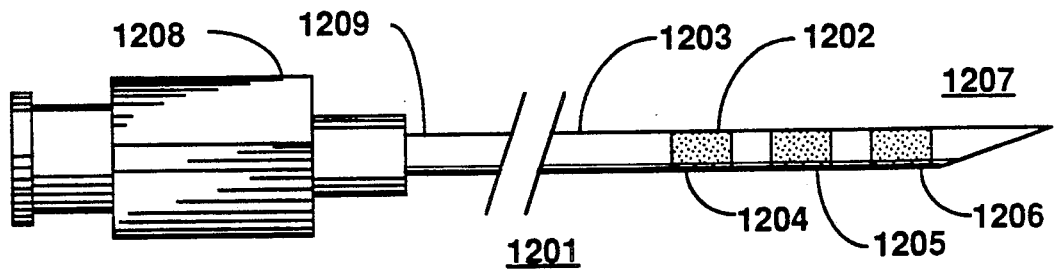
Fig. 12
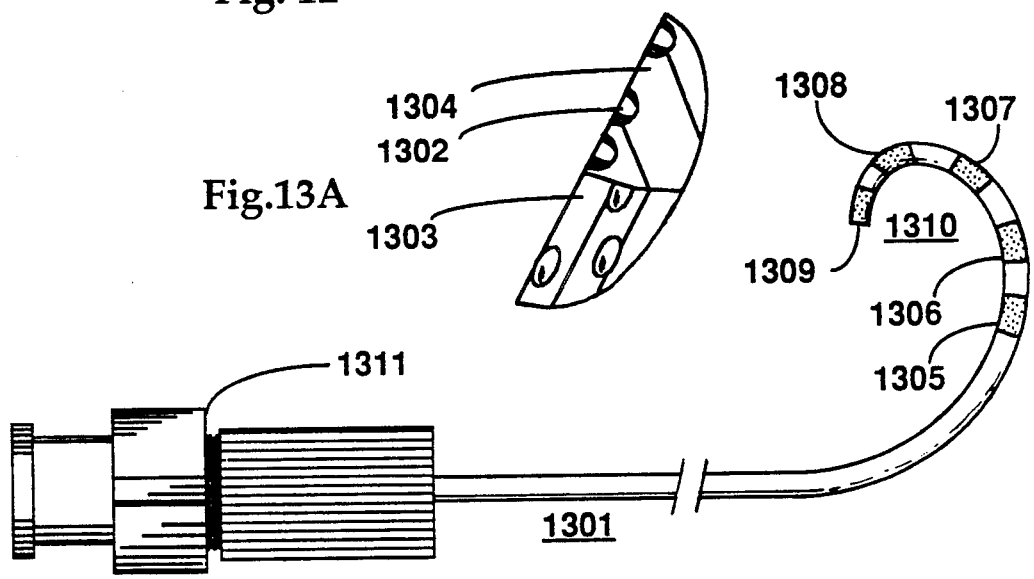
Fig.13A
Fig.13
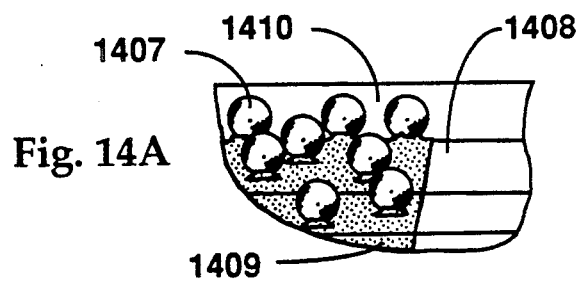
Fig. 14A
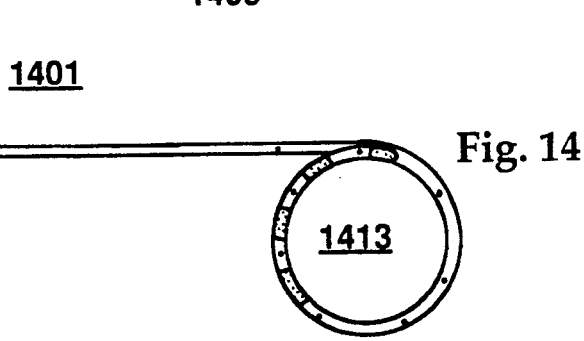
Fig. 14

ECHOGENIC DEVICES, MATERIAL AND METHOD

CROSS-REFERENCE TO RELATED APPLICATION

This application is a continuation-in-part of application Ser. No. 07/320,967, filed Mar. 9, 1989, entitled "Echogenic Devices, Material and Methods."

TECHNICAL FIELD

This invention relates generally to echogenic devices and methods and particularly to echogenic devices, material and methods, which among other applications may be used with medical devices that are insertable into a medium such as biological tissue and imageable with sonic imaging equipment.

BACKGROUND OF THE INVENTION

Ultrasonic imaging in the medical field is widely used for a variety of applications. In addition to imaging physiological structures and tissue such as organs, tumors, vessels, and the like, it is often desireable for a physician or technician to have an image of a medical device which has been inserted into the tissue or passageway of a patient. The types of devices which are surgically sterilized and inserted into patients are many. Typical examples include: needles, catheters and a variety of other medical products such as stents, dilators, pacing leads, introducers, angiography devices, angioplasty devices, pacemakers, in-patient appliances such as pumps and other devices. Various approaches have been used to enhance ultrasonic imaging by modifying the reflective surface characteristics of these devices.

U.S. Pat. No. 4,401,124 to Guess et al. discloses a system for reflection enhancement of a biopsy needle showing grooves cut in the tip of the needle. The reflection coefficient of the needle is enhanced by the use of a defraction grading disposed on the surface of the needle. The defraction grading is formed by the substantially parallel grooves, where the distance between the depth of adjacent grooves is a function of the wavelength of the ultrasound imaging system and the angle of the incident beam with respect to the surface of the needle. The spaced grooves provide constructive interference of the beam, thereby yielding maximum reflection back along the line of the incident beam.

Although the Guess et al. system with its helical defraction grading around the tip of the needle, along with other needles having similar rings, may provide some degree of signal reinforcement along the axis of incident energy, the overall image is far from ideal. Further, needles of this type typically exhibit a marked loss of resolution as the needle is oriented away from an optimum angle relative to the incident ultrasound beam, which angle depends upon the particular ring parameters.

What is needed is a device which provides more accurate monitoring of a surgical instrument such as a needle inserted into the body, which does not require a specific angle of orientation for its efficiency, and which is inexpensive to manufacture.

Another system for enhancing the ultrasound image of a portion of a medical instrument is disclosed in U.S. Pat. application Ser. No. 194,861, filed May 17, 1988, and owned by the assignee of the present application.

Furthermore, medical devices exist in which radiopaque stripes or additives are utilized to make the medical device appear on an X-ray machine or other radiographic device. For example, U.S. Pat. No. 365,750 to Sheridan et al. discloses an X-ray type catheter having an X-ray opaque pigment on the catheter tube.

One disadvantage of some X-ray opaque medical devices is that there is a risk of the X-ray opaque material flaking or peeling off and remaining in the patient. Furthermore, with these X-ray opaque paints and with the outer surface treatment utilized in the ultrasonic imaging device, fabrication expenses are increased.

SUMMARY OF THE INVENTION

The foregoing problems are solved and a technical advance is achieved with an illustrative echogenic medical device that is insertable into a medium such as the tissue or a passageway of a patient and imageable with sonic imaging equipment. The illustrative device includes an elongated member for insertion into a surrounding medium such as the biological tissue or passageway of a patient. The member includes a material having an acoustic impedance different from the acoustic impedance of the surrounding medium. The difference between acoustic impedances of the member material in the surrounding medium enhances an image produced in response to a sonic beam from the imaging equipment. The elongated member also includes an interface having a shape that is responsive to the sonic beam for producing the image.

As a departure in the art, the shape of the interface has been formed with a dimension that is less than a wavelength of the incident sonic beam. Furthermore, the shape advantageously includes a dimension such as a radius of curvature which is much less than the wavelength of the sonic beam. In one embodiment of the device, the interface includes the outside surface of the elongated member material. In the surface is a plurality of partially spherical indentations for producing a scattered component of the image in response to the incident beam. This image is produced regardless of the incident beam angle of which prior art devices depend for producing a reflected or constructive interference image. Advantageously, the scattered component of the image is produced when the radius of the partially spherical indentations or a dimension of another geometric shape or surface are much less than the wavelength of the incoming sonic beam. The difference in the acoustic impedances of the member material and surrounding medium enhances the intensity of the scattered component of the image.

In another illustrative embodiment of the device, the elongated member includes a substance such as a plurality of spherically or other geometrically-shaped particles that have a predetermined contour for establishing the interface. This contoured substance is contained within the material of the elongated member or alternatively or in combination attached to or embedded in the outside surface of the member material. In one case, the member material comprises a plastic for surrounding spherically-shaped glass particles. In another case, the glass particles are attached to the outside surface of the member with an adhesive material. In still another case, the particles are embedded in the outside surface of the member material. In still another illustrative embodiment, the contoured substance such as the glass particles are affixed to the outside surface of a stainless steel member using, for example, another material such as silver solder. In such instance, the substance has an acoustic impedance different from at least one of the impedances of the member material and surrounding tissue for enhancing the image produced in response to the sonic beam. The silver solder also presents another acoustic impedance to enhance an image.

The present invention also includes a method for sonically imaging an echogenic medical device in biological tissue. The method includes selecting a device having an acoustic impedance different from the acoustic impedance of the biological tissue. A difference between the impedances of the device and tissue enhances the image produced in response to a sonic beam from sonic imaging equipment. The method further includes inserting into the tissue an elongated member of the device including an interface having a shape responsive to the sonic beam for producing the image. As previously suggested, the shape includes a plurality of at least partially spherical indentations having a dimension less than a wavelength of the sonic beam. In particular, the radius of the indentations is much less than the wavelength of the sonic beam for producing a scattered component of the image. Also included in the method is directing a sonic beam toward the elongated member when inserted in the tissue and receiving the image produced from the interface in response to the sonic beam.

Another method of the present invention includes manufacturing the echogenic medical device for insertion into biological tissue and imageable with sonic imaging equipment. The illustrative manufacturing method includes forming an elongated member of the device from a material such as stainless steel or plastic having a predetermined acoustic impedance different from the acoustic impedance of the biological tissue. The difference between the acoustic impedance of the elongated member material and the biological tissue enhances an image produced in response to a sonic beam from the imaging equipment. Advantageously, the greater the difference between the member material and the biological tissue, the greater the enhancement of the image produced. The method also includes forming an interface in the member for producing the image in response to the beam. The interface, again having a shape with a dimension less than a wavelength of the sonic beam. In one embodiment, the outside surface of the elongated member material is indented with partially-spherical projections for producing a plurality of at least partially spherical indentations. In another embodiment, the method includes forming the interface by attaching a plurality of at least partially spherical particles to the surface of the elongated member. The particles having an acoustic impedance having at least said predetermined difference between at least one of the two impedances of the elongated member and biological tissue. A preferred diameter for the partially-spherical indentations is in the range of between 1-50 microns.

In another aspect of the invention, the echogenic device comprises an elongated body member including a composite material echogenically imageable. The composite material includes a formable matrix material with discrete sound reflective particles made from a material different from and more sonically reflective than the matrix material being embedded in the matrix material to enhance the echogenicity of the body member. Accordingly, the present invention provides a superior product which is readily manufactured and is reliable in use. Furthermore, the present invention may easily be made biological inert and sterile for patient safety.

Although the present invention has many applications, it is particularly envisioned to be useful in medical devices such as catheters, stents, and other products which are inserted into the tissue or passageway of a patient. These advantages are provided by forming the device, such as a catheter, from a composite material which includes a formable matrix material having discrete sound reflective particles embedded therein. In the preferred embodiment, the matrix material consists of polyethylene. The discrete sound reflective particles embedded therein are preferably glass microspheres having a diameter of about 5 microns. This composite material still maintains the requisite flexibility for many medical applications, while providing echogenicity throughout the body of the device. In this way, the physician may observe a full image of the medical device in the patient.

Furthermore, these advantages may be combined by including in the composite material a radiopaque material such as barium or tungsten to provide imaging with radiographic equipment. These advantages may be incorporated without a significant modification to the fabrication technique presently being used. The reflective particles, and optionally the radiopaque material, are mixed into the matrix material prior to forming the device by, for example, extrusion in the case of most catheters. Thus, no additional post extrusion fabrication steps are required to provide the desired echogenicity and a high level of quality control may be maintained.

Another aspect of the present invention includes a method of sonically imaging the device. This method includes providing an echogenic body member including composite material echogenically imageable, the composite material including a formable matrix material with discrete sound reflective particles made from a material different than and more sonically reflective than a matrix material being embedded in the matrix material to enhance the echogenicity of the body member; positioning the echogenic body member in a sonic imaging beam; and generating an image of the echogenic body member including the sound reflective particles from the sonic imaging beam.

One object of the present invention is to provide an improved echogenic device and materials.

Another object of the present invention is to provide an improved method of fabricating and of using echogenic devices.

Another object of the present invention is to provide improved catheters, dilators, stents, pacing leads and other appliances to be surgically inserted into medical patients.

Another object of the present invention is to provide a device, and a method of fabricating a device, which is both sound reflective and radiopaque for use with either ultrasonic equipment or with radiographic equipment. These and other objects and advantages of the present invention will be apparent from the specification and the drawings.

BRIEF DESCRIPTION OF THE DRAWINGS

FIGS. 11, 11A are a partial view of the distal end of yet another illustrative embodiment of the medical device of the present invention;

FIG. 12 is a partial view of a needle embodiment of the present invention;

FIGS. 13, 13A are a partial view of a catheter embodiment of the present invention; and FIGS. 14, 14A are a partial view of a stent embodiment of the present invention.

DETAILED DESCRIPTION

Figure 1:
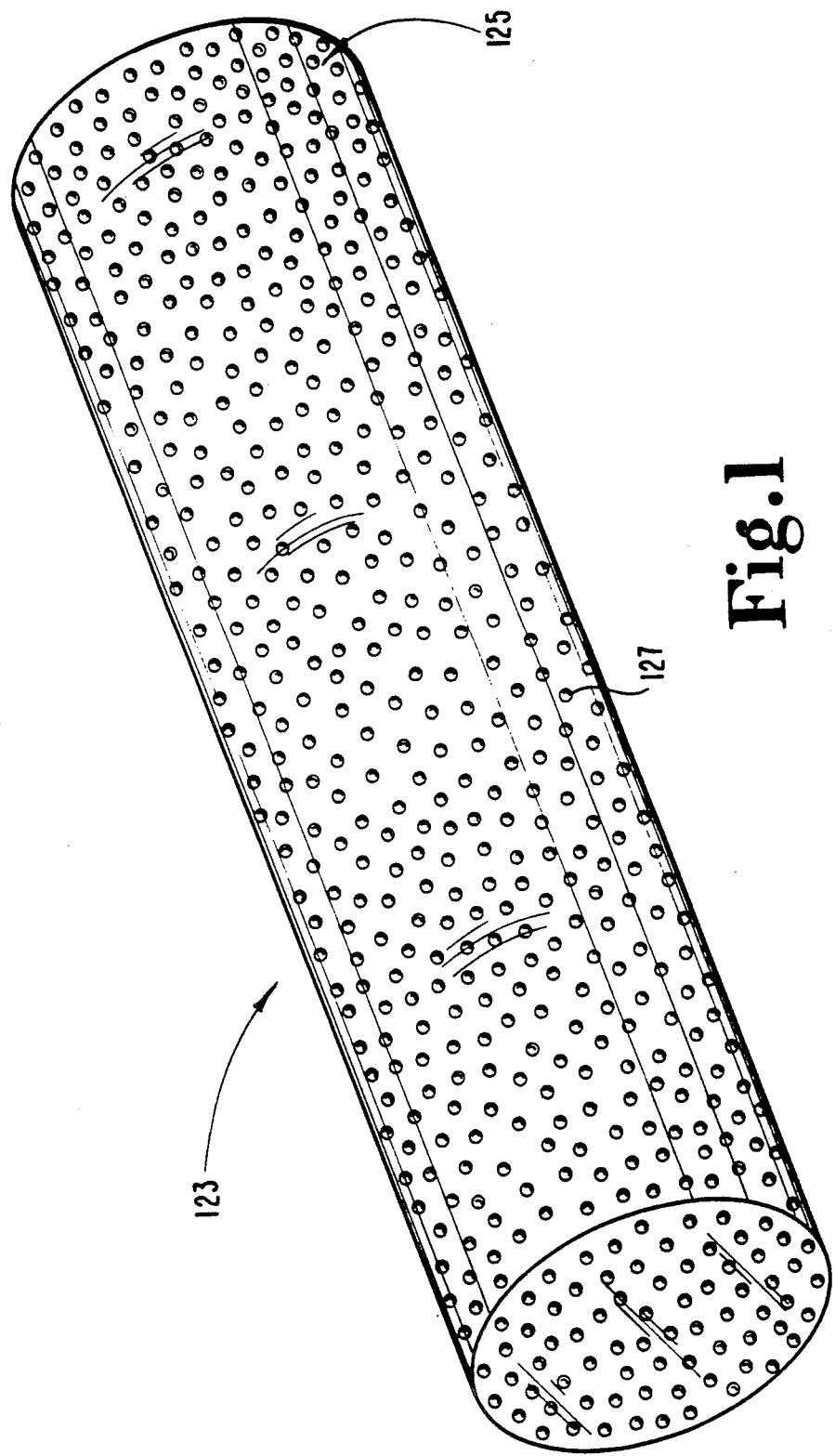
FIG. 1 is a perspective view of a first embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device and method, and such further applications of the principles of the invention as illustrated therein being contemplated as would normally occur to one skilled in the art to which the invention relates.

Referring to FIGS. 1-14, various embodiments of the present invention are illustrated, each embodiment having a different number in the hundreds digit. Accordingly, there is a "100" series, a "200" series, . . . , a "1300" series, and a "1400" series.

Referring to FIG. 1, a first embodiment of the present invention is shown. Echogenic body member 123 is a part of an echogenic device to be sonically imaged. The present invention may be utilized in a multitude of devices including medical devices, the following being only a set of possible examples: catheters, devices made from catheters, stents, pacing leads, introducers, pacemakers, ultrasonic rulers, in-patient appliances such as pumps, balloons, dilators, endoscopes, sphincterotomes, angiographic equipment, surgical implants, and other such devices. Echogenic body member 123 is at least partially made up of a composite material which is echogenically imageable in the patient, such as by the use of ultrasonic imaging equipment. The composite material includes matrix material 125 with discrete sound reflective particles 127 embedded in matrix material 125. Preferably, matrix material 125 is a plastic. Examples of suitable plastics may include urethane, ethylene, silicone, polyethylene, tetrafluorethylene. Preferably, matrix 125 is a formable, pliable material which may be molded and/or extruded to a variety of shapes, depending upon a specific application.

The sound reflective particles 127 are embedded in matrix material 125. Particles 127 are preferably made of a hard material, and it has been found that small glass particles are especially well suited for this application. Specifically, glass particles having a generally spherical shape forming glass microspheres are very suitable. Glass microspheres with an outer diameter of about 5 microns is one acceptable size. Other sized particles may be utilized as, for example, ranging between 1 and 50 microns and beyond. Furthermore, the particles do not necessarily have to be spherical, or may be partially spherical, although it is believed that spherical geometry for particles 127 is preferred. Furthermore, a partially spherical surface may be provided on the outside and/or the inside of particles 127, as for example a particle with a hollow spherical space therein. Particles 127 are made up of a different material than matrix 125. It is believed that the spherical shape provides for sound reflections at a variety of angles regardless of the direction from which the ultrasonic sound waves are emanating from, and accordingly, are more likely to reflect at least a portion of the transmitted signal back to the ultrasonic receiver to generate an image. Since many of the matrix materials available are relatively ultrasonically transparent in a patient, sound reflective particles 127 provide adequate reflection. The use of a composite, rather than a solution, provides adequate size for acoustic reflection off of the discrete particles embedded in the matrix. As indicated, a variety of materials may be utilized for the sound reflective particles, such as aluminum, hard plastic, sand, metal particles, and the like. Additionally, liquids, gases, gels, microencapsulants, and/or coacervates suspended in the matrix may alternatively be used either alone or in combination, so long as they form a composite with ultrasonically reflective particles in the matrix. Of this variety, glass balls have been found to be very well suited. For example, one commercially available supply of glass microspheres used for particle blasting is offered by Potters Industry, 377 Route 17, Hasbrouck Heights, N.J., U.S.A.

Another application is to have the matrix 125 compromise solder used to fuse parts together. For example, the solder matrix with sound reflective particles therein may be used to solder wires together in medical baskets (not shown) used to remove stones and other objects from medical patients. In addition to removal baskets, this technique may be used for other devices such as blood clot filters, guide wires and the like.

Figure 9A:
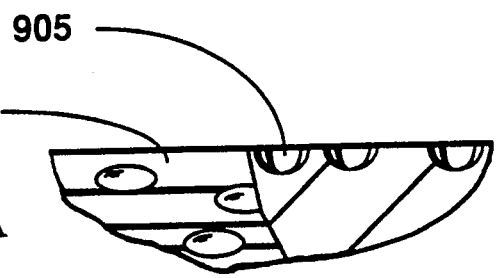
FIGS. 9, 9A are a partial cross-sectional view of another illustrative embodiment of the medical device of the present invention.
Figure 9:
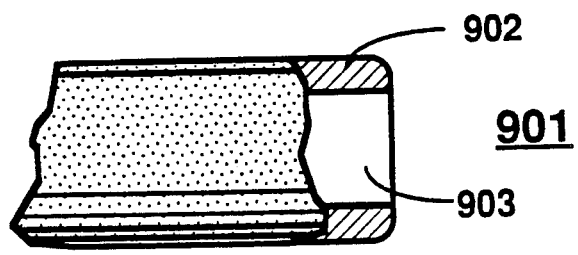

Depicted in FIG. 9 is a partial cross-sectional view of another illustrative embodiment of an echogenic medical device 901 that is insertable into a medium such as biological tissue or a passageway of a patient and that is sonically imageable with well-known sonic imaging equipment. As shown, medical device 901 comprises an elongated tubular member 902 with a passageway 903, commonly known as a lumen, extending longitudinally therein. Member 902 is part of any well-known catheter, stent, needle, and the like for insertion into a surrounding medium such as the biological tissue or passageway of a patient. The elongated member comprises a material having a first characteristic impedance, also referred to as acoustic impedance, different from the characteristic or acoustic impedance of the surrounding medium. Approximate values of characteristic or acoustic impedances for a variety of materials, both non-biological and biological are disclosed in Table 1.4 of Wells, *Physical Principles of Ultrasonic Diagnosis*, Academic Press, London, New York, 1969, p. 10, and in Table 3.1 of McDicken, *Diagnostic Ultrasonics: Principle and Use of Instruments*, John Wiley & Sons, New York, 1976, p. 43. A mean characteristic impedance value for human tissue is indicated as $1.63 \times 10^6$ MKS rayl. Another table of characteristic impedances of various solids, liquids, and gasses are listed in Kinsler et al., *Fundamentals of Acoustics*, 2nd Edition, John Wiley & Sons, Inc., New York, 1962, pp. 502-503. The difference between the characteristic impedance of the member material and the surrounding medium enhances the intensity of an image produced in response to a sonic beam emitted from sonic imaging equipment. The magnitude of the difference is proportional to the enhancement factor. A more detailed discussion is found in Chapter III of the McDicken reference.

In one embodiment of medical device 901, elongated member 902 comprises a plastic material. From the Kinsler and Wells references, soft plastic such as polythene is listed as having a characteristic impedance of $1.84 \times 10^6$ MKS rayl. A hard plastic such as Lucite in bulk form is listed as having a characteristic impedance of $3.2 \times 10^6$ MKS rayl. When device 902 is inserted into the tissue or passageway of a patient, the difference in impedance between the tissue of the patient and the plastic material of the device is sufficient to enhance an image produced in response to a sonic beam from imaging equipment. Medical device 901 also includes an interface including outside surface 904 having a shape responsive to a sonic beam for producing one component such as a reflective component of the sonic image. The outside surface of the elongated member also includes a plurality of partially spherical indentations 905 therein. These partially spherical indentations scatter the sonic beam to produce another component of the image. A dimension of 2.5 microns is one acceptable size for the radius of partially spherical indentations 905. The radius of the indentations may range, for example, between 0.5 and 25 microns and beyond. This radial dimension is related to the wavelength of the incoming sonic beam in a predetermined manner such that the radius is much less than the wavelength of the beam. For example, a sonic beam emitted at 3.5 MHz has a wavelength of approximately 17,700 microns, whereas a sonic beam emitted at 7.5 MHz has a wavelength of approximately 8,200 microns. Both of these frequencies are emitted from commercially available ultrasonic imaging equipment.

The partially spherical indentations provide a curved surface from which the incident sonic beam may be scattered to produce the desired image regardless of the angle of incidence with respect to outer surface 904.

The image produced by the interface including the outer surface and partially spherical indentations includes one or more components. When the dimensions of an object such as the partially spherical indentations are very much less than the wavelength of the sonic beam, Rayleigh scattering occurs. One known example of Rayleigh scattering is the interaction of ultrasound with blood cells. As discussed in Chapter III of the McDicken reference, the intensity of the scattered wave depends on the acoustic impedance change at the interface, the dimensions of the interface and the wavelength of the sonic beam. The amplitude of the scattered wave component is proportional to the square of the frequency of the sonic beam. Therefore, high frequency sonic beams are scattered the most strongly. For a reflection component to occur, dimensions of the reflecting surface must be greater than several wavelengths of the incident sonic beam. A refraction component is also produced when the incident beam propagates through the interface with a change in direction governed by well-known Snell's law.

Depicted in FIG. 12 is a partial view of medical needle 1201 which is one embodiment of the present invention. The needle has partially spherical indentations 1202 in outer surface 1203 of tubular stainless steel cannula 1209. The indentations are grouped together in three millimeter bands 1204-1205 spaced approximately two millimeters apart about the distal end 1207 of the needle. A commercially available connector 1208 is positioned at the proximal end of the needle.

Depicted in FIG. 13 is a partial view of medical catheter 1301 which is another embodiment of the present invention. This catheter embodiment also has partially spherical indentations such as 1302 in outer surface 1303 of flexible plastic material cannula 1304. This is just another example of the use of partially spherical indentations formed in the outer surface of an elongated member of a medical device as described with respect to FIG. 9. To ultrasonically image the catheter, three millimeter bands 1305-1309 of the indentations are grouped together and spaced approximately two millimeters apart about distal end 1310. The exploded view of band 1308 and cross-sectional cannula 1304 more clearly exhibits partially spherical indentations 1302 in outer surface 1303. A commercially available connector 1311 is attached to the proximal end of the catheter.

The interface as depicted in FIG. 1 includes the generally spherical surface produced by the generally spherical particles 127 and matrix material 125. In such example, the generally spherical particles comprise glass, which has a characteristic or acoustic impedance ranging from 12.0 to $12.9 \times 10^6$ MKS rayls as indicated by the Kinsler reference. The acoustic impedance difference between the plastic matrix material 125 and the glass particles 127 is much greater than that of the plastic and tissue, thereby enhancing the scattered component of the image produced by the spherical surfaces. The surrounding medium includes the matrix material.

From another aspect, the matrix material is considered the member material having a first acoustic impedance, whereas the glass particles are considered a substance having a predetermined contour for establishing the interface. The particles are included within the member material and either embedded in or attached to the surface of the elongated member of the device. In such case, the glass particles have a third acoustic impedance different from the acoustic impedance of the matrix material and surrounding biological tissue when inserted therein.

In another embodiment of medical device 905, elongated tubular member 902 comprises a stainless steel material having an acoustic or characteristic impedance in the range of 39.0 to $51.5 \times 10^6$ MKS rayls. Again, the outer surface of the elongated member includes a plurality of partially spherical indentations 905. Since the acoustic impedance difference between the stainless steel material and the surrounding tissue is even greater than that of glass or plastic and tissue, the intensity of the scattered component of the image produced from the partially spherical indentations is further increased.

The method of manufacturing medical device 901 includes forming the elongated member of the device from a material such as stainless steel or plastic as previously discussed, which has an acoustic impedance different from the biological tissue or medium in which the member is to be inserted. The interface is produced in one of several different manners. First, the elongated member may be extruded from one material and the partially spherical indentations formed or embossed in the material as the elongated member is being, for example, extruded. This would include the use of a well-known roller dye for selectively engaging the extruded material at designated positions. The dye would include at least partially spherical projections having the desired predetermined radius to form the indentations in the extruded material.

Figure 10A:
FIGS. 10, 10A are a partial view of still another illustrative embodiment of the medical device of the present invention.
Figure 10:
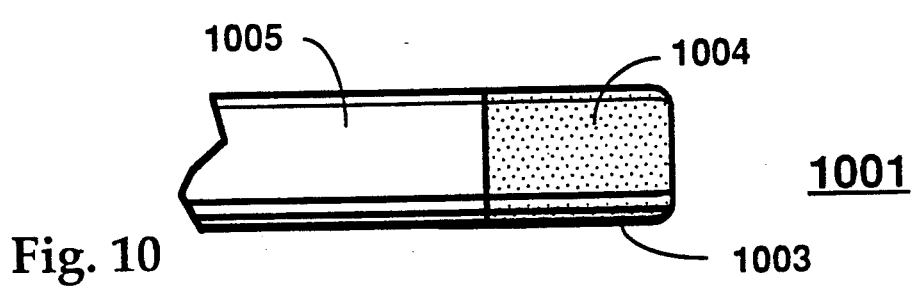

Depicted in FIG. 10 is a partial view of another illustrative embodiment of medical device 1001. A plurality of generally spherical particles 1002 consisting of, for example, glass may be attached to elongated tubular member 1003 using, for example, a well-known adhesive 1004. In such example, the elongated tubular member comprises any one of a plurality of well-known plastics having a flexibility or stiffness required for insertion into the tissue or passageway of the patient. In another embodiment of medical device 1001 of FIG. 10, spherical glass particles 1002 may be attached to a stainless steel tubular member using, for example, well-known silver solder. In such instance, the acoustic impedance of the glass particles as well as the silver solder may be considered in enhancing the produced image from an incident sonic beam.

Depicted in FIG. 14 is a partial view of medical stent 1401 having curled ends 1402 and 1403 for positioning the stent in a body passageway such as the ureter. The elongated plastic tubular member 1404 of the stent includes a plurality of ports 1405 for passing fluid therethrough. Similar to the configuration described with respect to FIG. 10, several bands 1406 of glass particles 1407 are attached to surface 1408 of the tubular member using a well-known medical grade adhesive 1409. Alternatively, the glass particles are embedded in a matrix material that forms the plastic tubular member. The bands are approximately three millimeters in width and positioned approximately two millimeters apart at ends 1402 and 1403. The bands of glass particles may also be spaced along the entire length of the tubular member. The glass particles form an interface that is imageable with sonic imaging equipment. To provide a smooth outer surface for inserting the stent, a layer of plastic material 1410 coats the particles and surface 1408.

Figure 11:
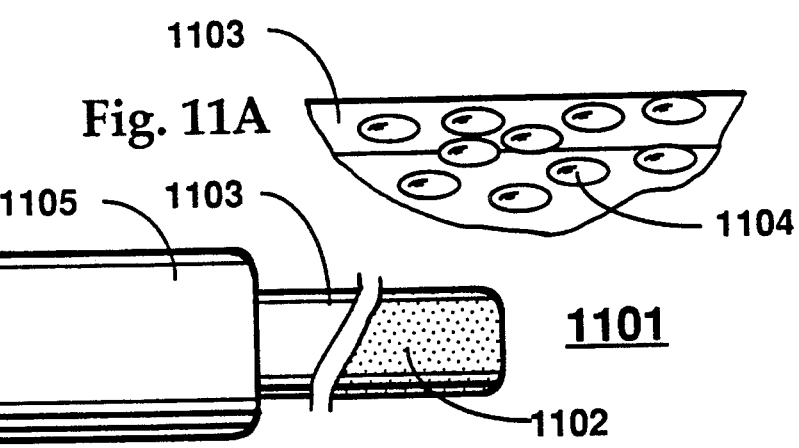

Depicted in FIG. 11 is another illustrative embodiment of an echogenic medical device 1101 for insertion into biological tissue and imageable with sonic imaging equipment. Medical device 1101 comprises an elongated member such as cylindrical rod or stylet wire 1102 that is inserted into a passageway or lumen of catheter 1005 for inserting and guiding the catheter into a passageway or blood vessel of a patient. The outside surface 1103 of the rod includes a plurality of partially spherical indentations 1104 for producing an image in response to a sonic beam from imaging equipment. Elongated member includes a material such as stainless steel with an acoustic impedance for enhancing any image produced by the partially spherical indentations in surface 1103. The elongated rod may be inserted into the lumen or passageway of a smooth outer surface catheter and inserted into a vessel of the patient and guided through the vessel with the assistance of the image produced by the indentations of the rod. The image produced by the indentations assists the physician in guiding the catheter and elongated rod through the passageway of the patient. This methodology includes directing a sonic beam toward the passageway of the patient with the device inserted therein and receiving an image from the indentations of the rod. Again, the material of the rod is selected to have an acoustic impedance different from that of the surrounding medium. It is envisioned that this surrounding medium may include body fluids from the patient or air which has an acoustic impedance of approximately 428 MKS rayls.

Figure 2:
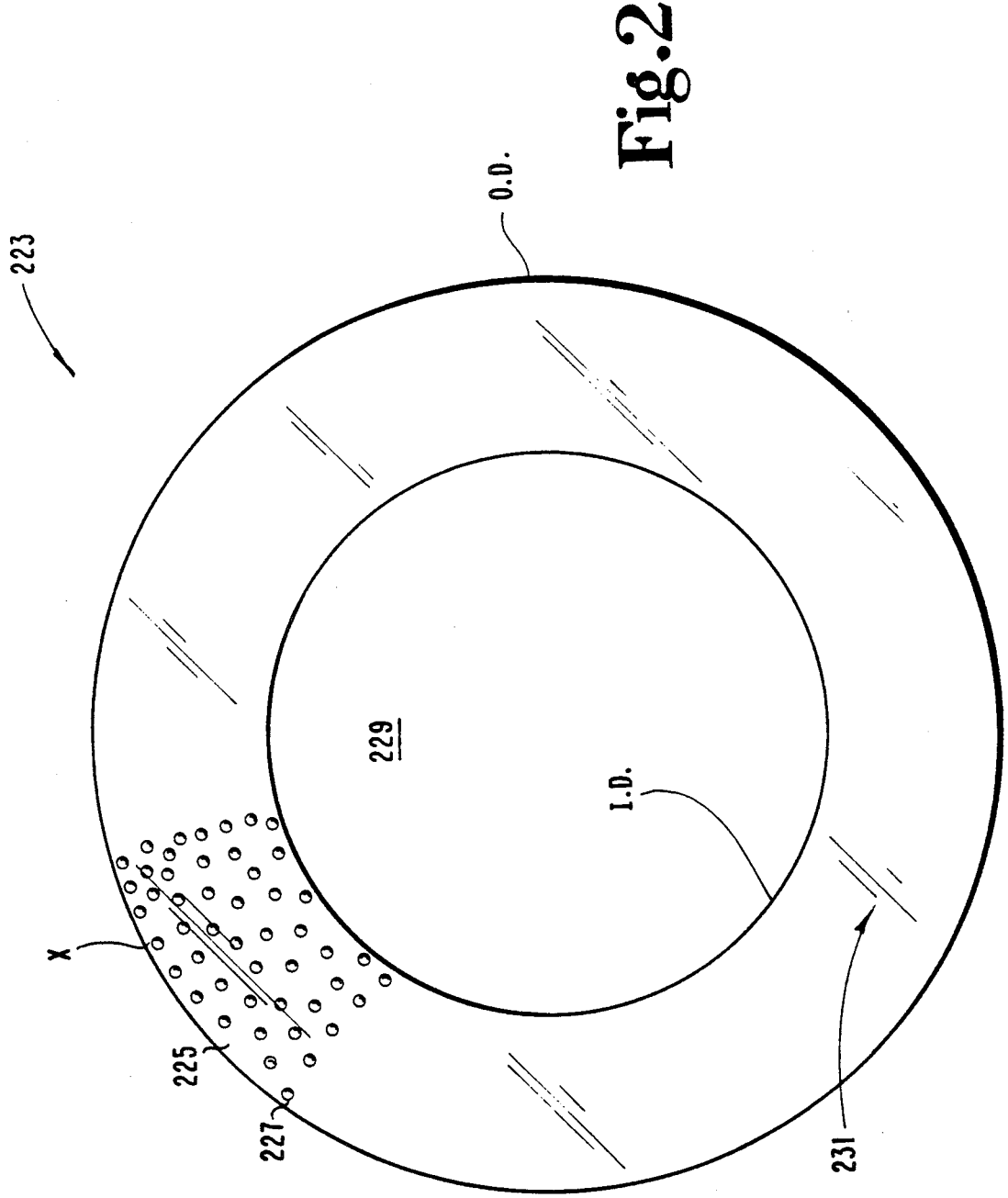
FIG. 2 is a cross-sectional view of a second embodiment of the present invention.

FIG. 2 discloses a second embodiment of the present invention setting forth one of many shapes or embodiments the present invention may include, in this case a catheter. Echogenic body member 223 forms a catheter with catheter wall 231 surrounding lumen 229. Lumen 229 has an inside diameter ID. In one embodiment, this internal diameter may be 0.040 inches. The outside diameter OD of echogenic body member 223 in this particular embodiment is 0.065 inches. The outside diameter X of one of the typical, illustrated microspheres in this particular embodiment is 5 microns, or 5 one-millionths of a meter. A typical reflective particle, sound reflective particle 227, is illustrated embedded in matrix material 225 similar to that previously described.

Figure 3:
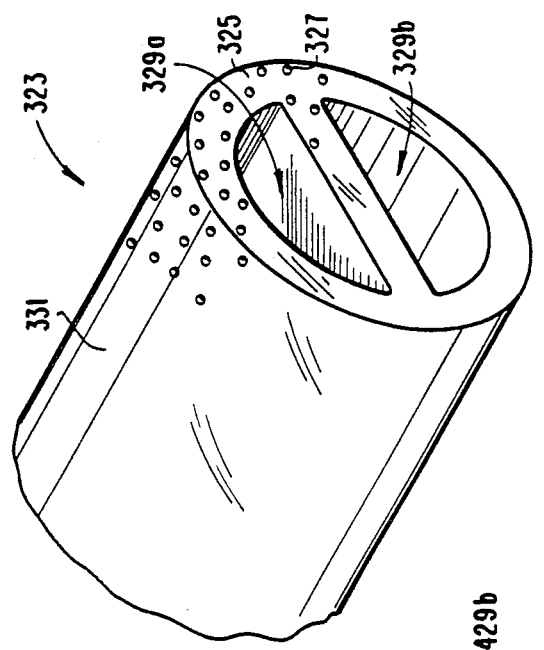
FIG. 3 is a cross-sectional perspective view of a third embodiment of the present invention.

Referring to FIG. 3, a third embodiment is shown with echogenic body member 323 being a two lumen catheter with lumen 329a and lumen 329b being disposed in catheter wall 331. A multitude of sound reflective particles are illustrated, such as sound reflective particle 327 embedded in matrix material 325.

Figure 4:
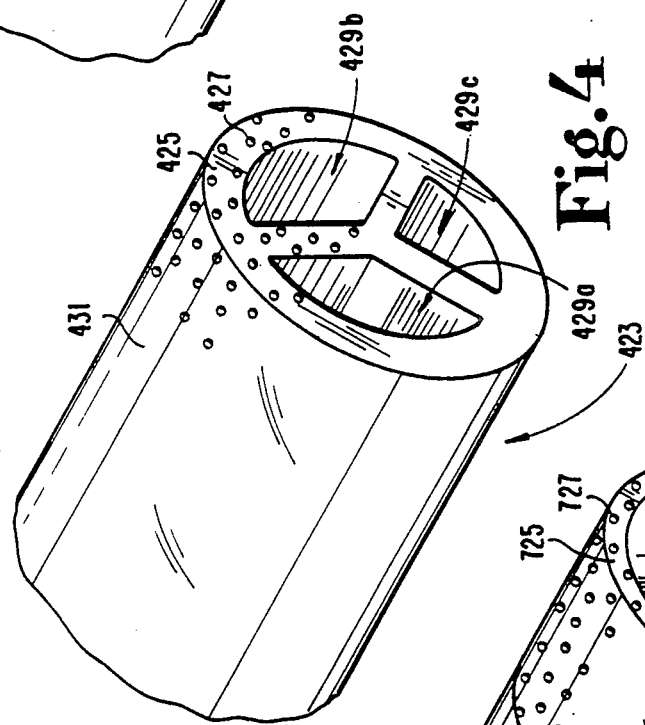
FIG. 4 is a cross-sectional perspective view of a fourth embodiment of the present invention.

Referring to FIG. 4, a fourth embodiment is illustrated as echogenic body member 423 which is a triple lumen catheter having lumen 429a, lumen 429b, and lumen 429c within catheter wall 431. Sound reflective particles, such as sound reflective particle 427 are shown in matrix 425.

Figure 7:
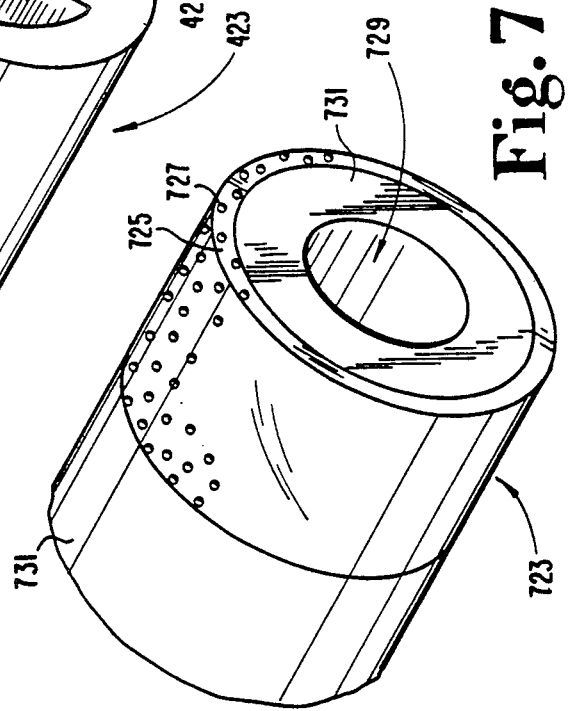
FIG. 7 is a cross-sectional perspective view of a fifth embodiment of the present invention.

Referring to FIG. 7, a fifth embodiment is shown with catheter wall 731 supporting echogenic body member 723. Member 723 is a composite as described above, with the matrix material being a painted on adhesive with sound reflective particles, such as particle 727, therein. Lumen 729 is in catheter wall 731. The sound reflective body is painted onto only a portion of the catheter as an annular stripe which is to be imaged.

Figure 8:
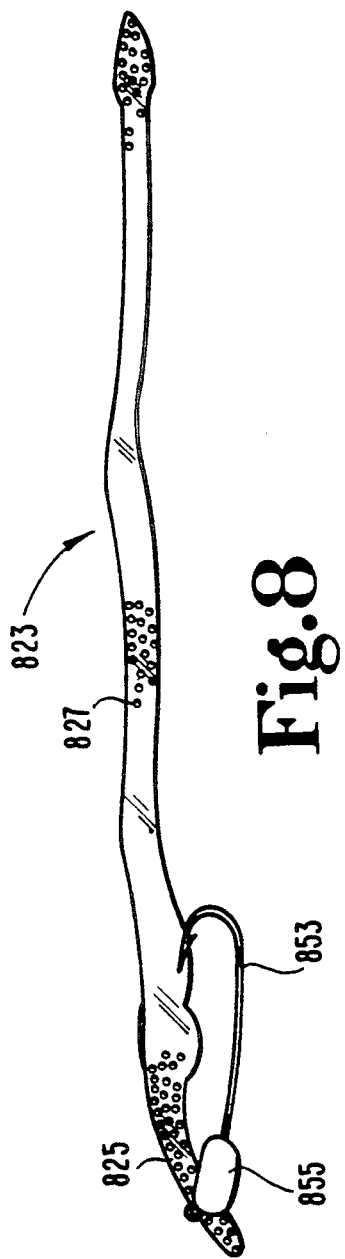
FIG. 8 is a side elevational view of a sixth embodiment of the present invention.

Referring to FIG. 8, echogenic body member 823 is in the form of a fishing lure, such as a plastic nightcrawler with metal hook 853 and sinker 855 popular with fisherman. Matrix material 825 is the plastic body of the worm with sound reflective particles, such as particle 827, therein. This is one of the many applications. Fisherman using a sonar type depth finder/fish finder may have enhanced imaging of lure 823 using the present invention.

As indicated, the foregoing embodiments are merely representative, and the present invention is not only restricted to medical devices. However, the benefits of the present invention are especially well suited for medical devices such as catheters.

The proportions between matrix material and the sound reflective particles may be measured by their percentage volume of the composite material. Typically, the composite material made up of between about 5% and 30% of the sound reflective particles by volume. One preferred embodiment has the composite material made up of about 10% of the sound reflective particles by volume. Another embodiment has about two to three percent sound reflective particles by volume. However, one percent or even a fraction of one percent, and up to 60% by volume of the sound reflective particles have been tested and determined to be acceptable for at least some applications. Nevertheless, as the percentage volume of the sound reflective particles increase, the amount of matrix material cohesively bonding the particles together is reduced. Accordingly, there ultimately occur trade-offs in terms of flexibility, durability, and cohesiveness. Furthermore, even ranges of less than 5% volume of sound reflective particles may be utilized in specific applications. Certain medical instruments such as an echogenic ruler may utilize the composite material of the present invention only in selected localized positions on the medical device. Such selected localization may include the use of only one, or only a few, sound reflective particles. The matrix material may be a glue or other compound which can be painted or otherwise applied to localized regions on the device where only that region of the device needs to be imaged echogenically (see e.g. FIG. 7). It is noteworthy that in at least certain applications, such as catheters, where the sound reflective particles comprise about 30% of the volume of the composite material, no significant loss in tensile strength was detected.

Figure 5:
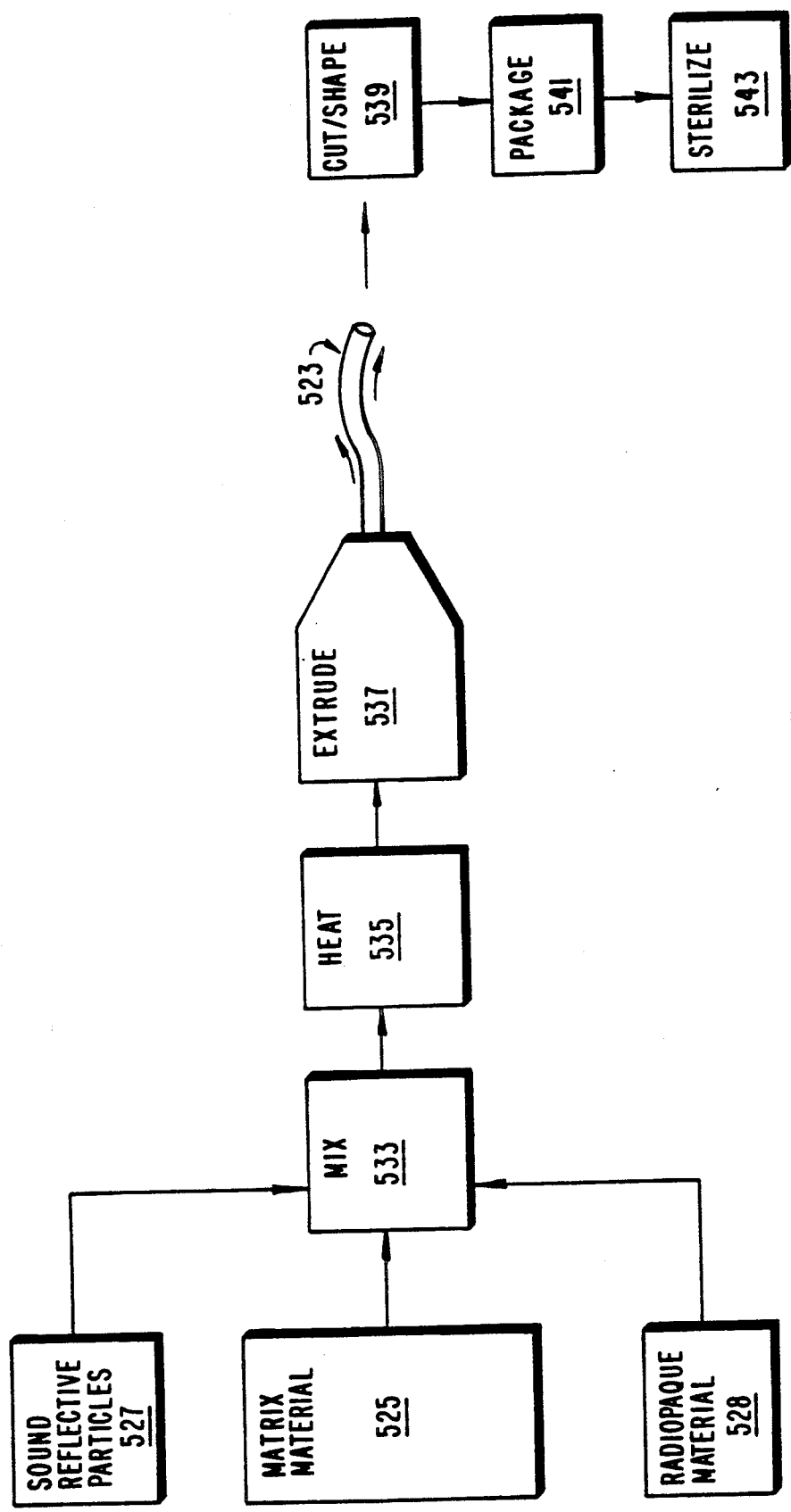
FIG. 5 is a schematic diagram of a method of fabrication according to the present invention.

Referring to FIG. 5, a schematic diagram of at least one method of fabricating the present invention is illustrated. Matrix material 525 may comprise plastic pellets which may be mixed with sound reflective particles 527 in the mixing step 533. Mixing may occur by gravity feed of the parts to be mixed into a screw or worm-gear type mechanism well known in extruder machines such as are used for catheter manufacture. Optionally, but not necessarily, radiopaque material 528 may also be mixed with the matrix material and the sound reflective particles. The radiopaque material may be one of numerous radiopaque materials already known, as for example, barium, bismuth or tungsten. The radiopacifier may be finely ground powder mixed during the mixing step 533. Before, during or after the mixing step 533 the mixture may be heated in the heating step 535. The heating maintains the matrix material in a molten or liquid state allowing it to be formed to the desired shape. During the forming step 537, which is illustrated as an extruding step known in the catheter industry, the composite mixture is formed into an echogenic body member 523, including the sound reflective particles from 527 embedded in the matrix material. As illustrated, echogenic body 523 is a tubular catheter body having a longitudinal lumen as previously described. Other types of forming may be used, such as molding or other such shaping. Thereafter, the echogenic body member may be cut and/or shaped, as for example, cut into a specified length and/or cutting side drainage lumens, curling, tapering, or other such processes known in the plastics industry and in the catheter industry. Thereafter, the medical device is packaged during the packaging step 541, preferably hermedically sealed as is known to maintain the medical device in a surgically sterile condition. Finally, the medical device may be sterilized during the sterilizing step 543, using heat, chemicals, or other known techniques.

Figure 6:
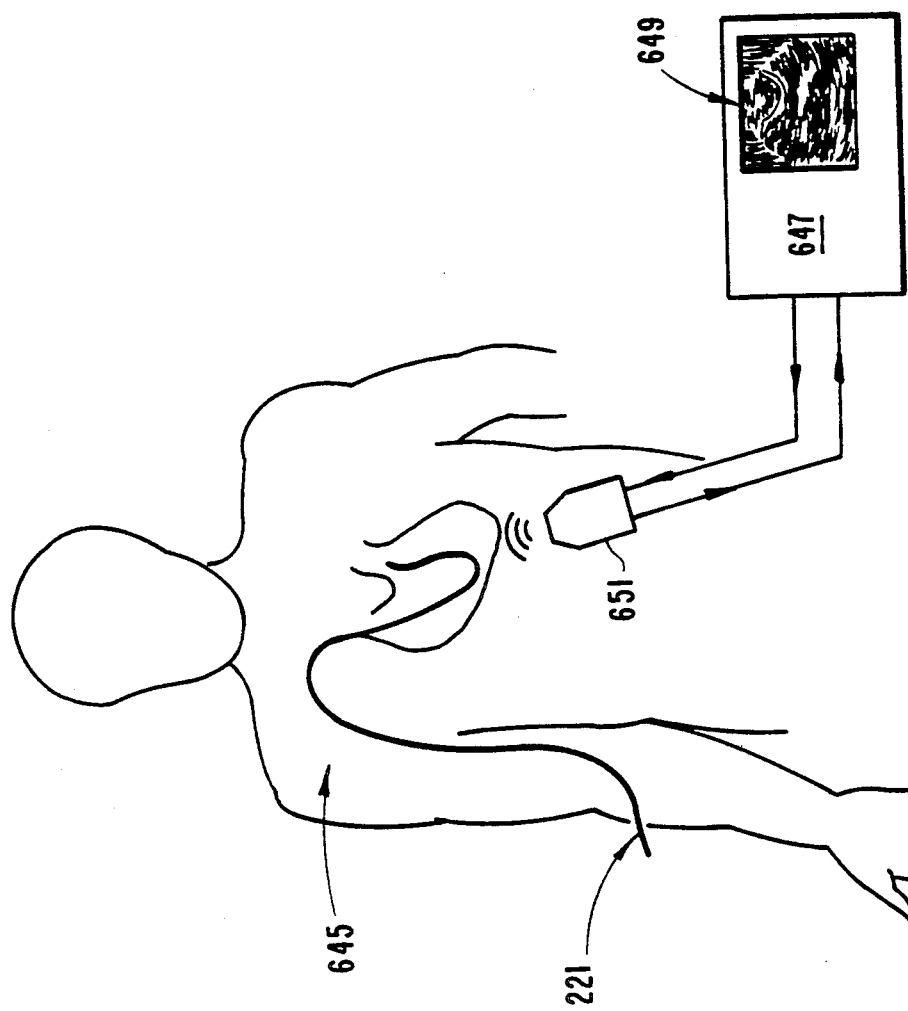
FIG. 6 illustrates one embodiment of the present invention inserted in a medical patient.

FIG. 6 shows an echogenic medical device 221 according to the present invention inserted surgically into medical patient 645. As illustrated in FIG. 6, a tubular catheter is utilized, it being understood that this is only one of many devices according to the present invention. Device 221 is sonically imaged using imaging device 647 with probe 651 to create image 649. This method of use involves placing a device according to the present invention in the sonic imaging beam or field of the probe as illustrated and using equipment, such as well known ultrasonic imaging equipment, to produce image 649.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. Although the particles have been described preferably a generally spherical or partially spherical in shape, the shape may include any geometric shape having one or more flat or curved surfaces having a dimension for producing a scattered component of the image. Naturally occurring crystalline structures are also contemplated.

What is claimed is:

1. A echogenic medical device insertable into a medium and imageable with sonic imaging equipment, comprising:
an elongated member for insertion into a surrounding medium, said member including a first material having a first predetermined acoustic impedance different from a second predetermined acoustic impedance of said medium, said first and second acoustic impedances having at least a predetermined difference therebetween, said member also including an interface responsive to said sonic beam for producing said image, including a particulate-type, discontinuous curved surface having a dimension less than a wavelength of a sonic beam from said equipment, whereby said difference between said first and second acoustic impedances and said curved surface cooperate in response to said sonic beam to produce an image of said member about said interface.

2. The device of claim 1 wherein said interface includes an outside surface of said member material.

3. The device of claim 2 wherein said curved surface includes at least a partially spherical indentation in said outside surface.

4. The device of claim 3 wherein said interface includes a plurality of said indentations and wherein each of said indentations has a radius of approximately said dimension.

5. The device of claim 1 wherein said member includes a substance having a predetermined contour for establishing said interface.

6. The device of claim 5 wherein said first material includes said substance therein.

7. The device of claim 5 further comprising a second material for affixing said substance to an outside surface of said first material.

8. The device of claim 7 further comprising a material forming a relatively smooth outer surface layer over said substance.

9. The device of claim 5 wherein said substance has a third predetermined acoustic impedance different from at least one of said first and second acoustic impedances, a second predetermined difference between said third impedance and at least one of said first and second impedances for enhancing said image.

10. The device of claim 5 wherein said first material comprises a plastic material.

11. The device of claim 10 wherein said substance comprises at least partially spherical particles.

12. The device of claim 11 wherein said particles comprise glass.

13. The device of claim 1 wherein said first material comprises stainless steel.

14. The device of claim 1 wherein said member includes a substance embedded in a surface of said member, said substance having a predetermined contour for establishing said interface.

15. The device of claim 14 further comprising a material for forming a relatively smooth outer surface layer over said substance.

16. An echogenic material device insertable into biological tissue and imageable with sonic imaging equipment, comprising:
an elongated member for insertion into said biological tissue having a second predetermined acoustic impedance, said member comprising a material having a first predetermined acoustic impedance different from said second impedance, said first and second acoustic impedances having at least a predetermined difference therebetween, said member including a surface having a plurality of discontinuous, at least partially spherical indentations, said indentations having a radius of curvature less than a wavelength of a sonic beam, whereby said difference between said first and second acoustic impedances and said indentation cooperate in response to said sonic beam to produce an image of said member about said interface.

17. The device of claim 16 wherein said material comprises stainless steel.

18. The device of claim 16 wherein said material comprises plastic.

19. A method for sonically imaging an echogenic medical device in biological tissue, comprising:
selecting said device including a material having a first predetermined acoustic impedance different from a second predetermined acoustic impedance of said biological tissue, said first and second acoustic impedances having at least a predetermined difference therebetween;
inserting into said tissue an elongated member of said device including an outer interface having a plurality of fixedly positioned, discontinuous, at least partially spherical surfaces, said surfaces having a dimension less than a wavelength of a sonic beam from sonic imaging equipment;
directing said sonic beam toward said elongated member when inserted in said tissue; and
receiving an image of said elongated member about said interface, whereby said difference between said first and second acoustic impedances and said surfaces cooperate in response to said sonic beam to produce said image of said member about said interface.

20. A method for manufacturing an echogenic medical device for insertion into biological tissue and imageable with sonic imaging equipment, comprising:
forming an elongated member of said device from a material having a first predetermined acoustic impedance different from a second predetermined acoustic impedance of said biological tissue, said first and second impedances having at least a predetermined difference, said member having an outer surface; and
forming an interface in said elongated member for producing said image in response to said beam, said interface having a plurality of fixedly positioned, discrete particulate-type, discontinuous, curved surfaces formed about said outer surface and having a dimension less than a wavelength of a sonic beam from said equipment, whereby said difference between said first and second acoustic impedances and said curved surfaces cooperate in response to said sonic beam to produce an image of said member about said interface.

21. The method of claim 20 wherein forming said interface includes producing a plurality of at least partially spherical indentations in an outside surface of said elongated member.

22. The method of claim 20 wherein forming said interface includes attaching a plurality of at least partially spherical particles to said elongated member, said particles having a third predetermined acoustic impedance having at least said predetermined difference between at least one of said first and second impedances.

23. The method of claim 22 wherein said particles have a diameter in a range of between one and fifty microns.

24. An echogenic device adapted to be imaged by sonic imaging equipment, comprising:
an echogenic body member including a composite material echogenically imageable, said composite material including a formable matrix material with discrete sound reflective particles made from a material different than and more sonically reflective than said matrix material being embedded in said matrix material to enhance the echogenicity of said body member.

25. The device of claim 24 wherein said echogenic body member is a medical device to be inserted inside a patient.

26. The device of claim 25 wherein said sound reflective particles have an at least partially spherical surface for providing sound reflections at a plurality of angles.

27. The device of claim 26 wherein said echogenic body member comprises a tubular catheter body having at least one longitudinal lumen within a catheter wall.

28. The device of claim 27 wherein said composite material is made up of between five percent and thirty percent of said sound reflective particles by volume.

29. The device of claim 28 wherein said composite material further includes a radiopaque material being radiographically imageable in a patient.

30. The device of claim 26 wherein said echogenic body member comprises a tubular catheter body having at least one longitudinal lumen within a catheter wall.

31. The device of claim 30 wherein said sound reflective particles comprise glass particles.

32. The device of claim 31 wherein said composite material is made up of between about five percent and thirty percent of said sound reflective particles by volume.

33. The device of claim 32 wherein said composite material further includes a radiopaque material being radiographically imageable in a patient.

34. The device of claim 33 wherein said sound reflective particles are microspheres having an outer diameter of about five microns.

35. The device of claim 34 wherein said composite material is made up of about ten percent of said sound reflective particles by volume.

36. The device of claim 35 wherein said radiopaque material is selected from a group consisting of barium and tungsten.

37. The device of claim 25 wherein said sound reflective particles have an at least partially spherical surface for providing sound reflections at a plurality of angles.

38. The device of claim 25 wherein said sound reflective particles comprise glass particles.

39. The device of claim 38 wherein said composite material is made up of between about five percent and thirty percent of said sound reflective particles by volume.

40. The device of claim 39 wherein said composite material further includes a radiopaque material being radiographically imageable in a patient.

41. The device of claim 25 wherein said composite material is made up of between about five percent and thirty percent of said sound reflective particles by volume.

42. The device of claim 25 wherein said composite material further includes a radiopaque material being radiographically imageable in a patient.

43. The device of claim 42 wherein said radiopaque material is selected from a group consisting of barium, bismuth and tungsten.

44. The device of claim 25 wherein said sound reflective particles are microspheres having an outer diameter of about five microns.

45. The device of claim 25 wherein said composite material is made up of about ten percent of said sound reflective particles by volume.

46. The device of claim 25 wherein said matrix material comprises polyethylene.

47. The device of claim 25 wherein said composite material is made up between about one percent and sixty percent of said sound reflective particles by volume.

48. The device of claim 25 wherein said sound reflective particles have an outer diameter of between one micron and fifty microns.

49. An echogenic device to be positioned within a medium and imageable with sonic equipment, said device comprising a body having an outer surface with image enhancing means for improving the sonic imaging of the device, characterized in that said means comprises fixedly positioned, discrete particulate type, discontinuous, acoustic discontinuities having a curved surface formed about or associated with the outer surface of the body.

50. A device according to claim 49 wherein the discontinuities are int he form of particles with an acoustic impedance different from that of the body, the particles being embedded within at least part of the body, partially embedded within at least part of the surface of the body, or disposed on at least part of the surface of the body.

51. A device according to claim 50 wherein the particles are hollow or are solid with the body thus being composite by nature.

52. A device according to claim 49 wherein the discontinuities are int he form of indentations in the surface of the body.

53. A device according to claim 52 wherein the body has an acoustic impedance different from the medium.

54. A device according to claim 49 wherein the discontinuities are disposed in a random manner relative to the body.

55. A device according to claim 49 wherein the discontinuities have a curved or multifaceted contour to effect ultrasonic scattering in a multiplicity of directions.

56. A device according to claim 49 wherein the particulate discontinuities each have a dimension substantially less than the wavelength to be used in the ultrasonic equipment.

57. A device according to claim 49 wherein the characteristic impedance of the body has a difference from that of the medium or biological tissue to achieve image enhancement, and wherein the characteristic impedance of the particles has at least said difference between the other characteristic impedances, the particles being more reflective than the material of the body.

58. A device according to claim 49 wherein the discontinuities have diameter(s) in the range of 1 to 50 microns.

59. A device according to claim 58 wherein the discontinuities are of glass and form between 5 and 60% by volume of the composite body.

60. An echogenic device adapted to be imaged by sonic imaging equipment, comprising:
an echogenic body member including a composite material echogenically imagable, said composite material including a solid matrix material other than a gel and discrete sound reflective particles fixedly positioned throughout said matrix material, ultrasonically different than tissue and more sonically reflective than said matrix material to enhance the echogenicity of said body member.

61. The device of claim 60 wherein said echogenic body member is a medical device to be inserted inside a patient.

62. The device of claim 60 wherein said sound reflective particles have an at least partially spherical surface for providing sound reflections at a plurality of angles.

63. The device of claim 60 wherein said sound reflective particles comprise glass particles.

64. The device of claim 63 wherein said composite material is made up of between about five percent and thirty percent of said sound reflective particles by volume.

65. The device of claim 64 wherein said composite material further includes a radiopaque material being radiographically imagable in a patient.

66. The device of claim 60 wherein said composite material is made up of between about five percent and thirty percent of said sound reflective particles by volume.

67. The device of claim 60 wherein said composite material further includes a radiopaque material being radiographically imagable in a patient.

68. The device of claim 67 wherein said radiopaque material is selected from a group consisting of barium bismuth and tungsten.

69. The device of claim 60 wherein said sound reflective particles are microspheres having an outer diameter of about five microns.

70. The device of claim 60 wherein said composite material is made up of about ten percent of said sound reflective particles by volume.

71. The device of claim 60 wherein said matrix material comprises polyethylene.

72. The device of claim 60 wherein said composite material is made up of between about one percent and sixty percent of said sound reflective particles by volume.

73. The device of claim 60 wherein said sound reflective particles have an outer diameter of between about one micron and fifty microns.

74. A method fabricating echogenic devices, comprising the steps of:

mixing a matrix material with discrete sound reflective particles made from a material different than and more sonically reflective than said matrix material to form a composite mixture;

heating said composite mixture to maintain said matrix material in a molten state; and forming said composite mixture with said particles fixedly positioned throughout said matrix material to form an echogenic body member including a composite material echogenically imagable in a patient.

75. The method of claim 74 wherein said forming step includes the step of extruding a pliable tubular catheter body having at least one longitudinal lumen within a catheter wall, said catheter body being echogenically imagable in a patient.

76. The method of claim 75 further comprising the step of sterilizing said catheter body to sterilize said catheter for use in a patient.

77. The method of claim 76 wherein said sound reflective particles comprise glass microspheres having an outer diameter of about five microns and wherein said composite mixture is made up of between about five percent and thirty percent of said sound reflective particles by volume.

78. The method of claim 74 wherein said sound reflective particles comprise glass particles.

79. The method of claim 74 wherein said composite mixture is made up between about five percent and thirty percent of said sound reflective particles by volume.

80. A method of sonically imaging a device, comprising:

providing an echogenic body member including a composite material echogenically imagable, said composite material including a solid matrix material other than a gel and discrete sound reflective particles fixedly positioned throughout said matrix material, ultrasonically different than tissue and more sonically reflective than said matrix material to enhance the echogenicity of said body member;

positioning said echogenic body member in a sonic imaging beam; and generating an image of said echogenic body member including said sound reflective particles from said sonic imaging beam.

81. The method of claim 80 wherein said echogenic body member is surgically sterilized and wherein said matrix material is a plastic and wherein said sound reflective particles are glass microspheres and wherein said positioning step includes the step of inserting said sterilized echogenic body member in a medical patient.

82. The method of claim 80 wherein said composite material is made up of between about five percent and thirty percent of said sound reflective particles by volume.

83. An echogenic device adapted to be imaged by sonic imaging equipment, comprising:

an echogenic body member including a composite material echogenically imagable, said composite material including a solid matrix material other than a gel and at least one discrete omni-directional sound reflective particle fixedly positioned in said matrix material, ultrasonically different than tissue and more sonically reflective than said matrix material to enhance the echogenicity of said body member at a selected location of said at least one omni-directionally sound reflective particle.

84. The device of claim 83 wherein said echogenic body member is a medical device surgically sterilized to be inserted inside a patient.

85. The device of claim 83 wherein said at least one omni-directionally sound reflective particle comprises at least one glass particle.

86. An echogenic device adapted to be imaged by sonic imaging equipment, comprising:

an echogenic body member comprising a medical device to be inserted inside a patient and including a composite material echogenically imagable, said composite material including a solid matrix material and discrete sound reflective particles fixedly positioned throughout, different than and more sonically reflective than said matrix material to enhance the echogenicity of said body member, said sound reflective particles having an at least partially spherical surface for providing sound reflections at a plurality of angles.

87. The device of claim 86 wherein said echogenic body member comprises a tubular catheter body having at least one longitudinal lumen within a catheter wall.

88. The device of claim 87 wherein said sound reflective particles comprise glass particles.

89. The device of claim 88 wherein said composite material is made up of between about five percent and thirty percent of said sound reflective particles by volume.

90. The device of claim 89 wherein said composite material further includes a radiopaque material being radiographically imagable in a patient.

91. The device of claim 90 wherein said sound reflective particles are microspheres having an outer diameter of about five microns.

92. The device of claim 91 wherein said composite material is made up of about ten percent of said sound reflective particles by volume.

93. The device of claim 92 wherein said radiopaque material is selected from a group consisting of barium and tungsten.

94. An echogenic device adapted to be imaged by sonic imaging equipment, comprising:

an echogenic body member including a composite material echogenically imagable, said composite material including a solid matrix material and discrete sound reflective particles fixedly positioned throughout, different than and more sonically reflective than said matrix material to enhance the echogenicity of said body member, said echogenic body member comprising a medical device to be inserted inside a patient and including a tubular catheter body at least one longitudinal lumen within a catheter wall.

95. The device of claim 94 wherein said composite material is made up of between five percent and thirty percent of said sound reflective particles by volume.

96. The device of claim 95 wherein said composite material further includes a radiopaque material being radiographically imagable in a patient.

97. A method of sonically imaging a device, comprising:

providing a surgically sterilized echogenic body member having at least one longitudinal lumen within a catheter wall and including a composite material echogenically imagable, said composite material including a solid matrix, plastic material and discrete sound reflective, glass microsphere particles fixedly positioned throughout, different than and more sonically reflective than said matrix material to enhance the echogenicity of said body member;

positioning said echogenic body member in a sonic imaging beam and inserting said sterilized echogenic body member in a medical patient; and generating an image of said echogenic body member including said sound reflective particles from said sonic imaging beam.

98. The method of claim 97 wherein said composite material further includes a radiopaque material being radiographically imagable in a patient.

* * * * *